United States Patent [19]
Taylor

[11] Patent Number: 6,008,432
[45] Date of Patent: Dec. 28, 1999

[54] METALLIC TEXTURE COATED PROSTHETIC IMPLANTS

[75] Inventor: Scott K. Taylor, Ridgewood, N.J.

[73] Assignee: Osteonics Corp., Allendale, N.J.

[21] Appl. No.: 08/942,278

[22] Filed: Oct. 1, 1997

[51] Int. Cl.$^6$ .............................. A61F 2/34; A61F 2/30; A61F 2/36; A61F 2/28

[52] U.S. Cl. .............................. 623/16; 623/18; 623/19; 623/20; 623/22; 623/23; 606/60; 606/76

[58] Field of Search .................................. 623/11, 16, 17, 623/18, 20, 19, 22, 23; 606/60, 69–70, 71, 76, 77

[56] References Cited

U.S. PATENT DOCUMENTS

| | | |
|---|---|---|
| 3,605,123 | 9/1971 | Hahn . |
| 4,164,794 | 8/1979 | Spector et al. ............................. 623/18 |
| 4,168,326 | 9/1979 | Broemer et al. ........................... 623/18 |
| 4,336,618 | 6/1982 | Raab . |
| 4,801,300 | 1/1989 | Kurze et al. . |
| 4,855,101 | 8/1989 | Mohs et al. . |
| 5,152,794 | 10/1992 | Davidson .................................. 623/16 |
| 5,258,030 | 11/1993 | Wolfarth et al. . |
| 5,263,986 | 11/1993 | Noiles et al. . |
| 5,370,694 | 12/1994 | Davidson . |
| 5,372,660 | 12/1994 | Davidson et al. . |
| 5,373,621 | 12/1994 | Ducheyne et al. ......................... 623/23 |
| 5,507,833 | 4/1996 | Bohn ......................................... 623/18 |
| 5,658,334 | 8/1997 | Caldarise et al. .......................... 623/16 |
| 5,665,118 | 9/1997 | LaSalle et al. ............................. 623/16 |

OTHER PUBLICATIONS

Stephen D. Cook et al. Fatigue properties of carbon–and porous–coated Ti–6A1–4V alloy. *Journal of Biomedical Materials Research,* vol. 18, 497–512 (1984).

David H. Kohn et al. A parametric study of the factors affecting the fatigue strength of porous coated Ti–6A1–4V implant alloy. *Journal of Biomedical Materials Research,* vol. 24, 1483–1501 (1990).

Debra Wolfarth et al. Parametric analysis of interfacial stress concentrations in porous coated implants. *Journal of Applied Biomaterials,* vol. 1, 3–12 (1990).

*Primary Examiner*—David J. Isabella
*Assistant Examiner*—Choon P. Koh
*Attorney, Agent, or Firm*—Arthur Jacob

[57] ABSTRACT

A layer of material is interposed between a metallic texture coating and the substrate of a component of a prosthetic implant, the layer being bonded to the substrate and, in turn, receiving the metallic texture coating so as to deter propagation of fatigue-induced cracks from the metallic texture coating into the substrate.

14 Claims, 1 Drawing Sheet

METALLIC TEXTURE COATED PROSTHETIC IMPLANTS

The present invention relates generally to the construction of prosthetic implants and pertains, more specifically, to structures and methods for improving the fatigue strength of metallic texture coated prosthetic implants.

It is common to provide components of a prosthetic implant, such as the femoral component of a hip replacement, with a metallic texture coating which provides a textured surface so as to attain the desired fixation between components of the prosthetic implant and the natural bone within which the components are implanted. It has been demonstrated, however, that such a metallic texture coating, while advantageous for fixation purposes, reduces the fatigue strength of the underlying substrate of the components at the location of the coating, as compared to the fatigue strength of uncoated portions of components. For example, an arc-deposited titanium currently used for establishing a desirable metallic texture coating on a titanium alloy substrate of a prosthetic implant component has been observed to reduce the fatigue strength of the substrate of the component at the location of the coating by as much as eighty-three percent. Various published studies have confirmed the deleterious effects of metallic texture coatings on the fatigue strength of prosthetic implants. The following are some of these published studies: (1) Steven D. Cook et al, "Fatigue Properties of Carbon- and Porous-Coated Ti-6Al-4V Alloy", Journal of Biomedical Materials Research, Vol 18, 497–512 (1984); (2) David H. Kohn et al, "A Parametric Study of the Factors Affecting the Fatigue Strength of Porous Coated Ti-6Al-4V Implant Alloy", Journal of Biomedical Materials Research, Vol 24, 1483–1501 (1990); and (3) Debra Wolfarth et al, "Parametric Analysis of Interfacial Stress Concentrations in Porous Coated Implants", Journal of Applied Biomaterials, Vol 1, 3–12 (1990).

The present invention provides a structure and a method for increasing the fatigue strength of metallic texture coated prosthetic implants. As such, the present invention attains several objects and advantages, some of which are summarized as follows: Enables increased longevity in prosthetic implants having metallic texture coated components; provides metallic texture coated components of prosthetic implants with an improved structure which enhances fatigue strength, as compared to metallic texture coated components without the improved structure; attains the advantages of metallic texture coated prosthetic implant components without a detrimental reduction in the fatigue strength of the components; enables the use of desirable metallic texture coatings and techniques, such as arc-deposited titanium coatings, for components of a prosthetic implant without sacrificing long-term performance; enables the use of a metallic texture coating at locations on an implant component not previously amenable to a metallic texture coating because of structural demands placed upon the component at those locations, thereby providing a wider choice of design options in the construction of implant components; provides a relatively simple technique for constructing a metallic texture coated prosthetic implant component heaving desirable fatigue strength characteristics.

The above objects and advantages, as well as further objects and advantages, are attained by the present invention which may be described briefly as an improvement for increasing the fatigue strength of a prosthetic implant component having a metallic texture coating on a substrate, the improvement comprising a layer of material interposed between the metallic texture coating and the substrate, and interposing the layer of material between the metallic texture coating and the substrate, the layer being bonded to the substrate and, in turn, receiving the metallic texture coating so as to deter propagation of fatigue-induced cracks from the metallic texture coating into the substrate.

The invention will be understood more fully, while still further objects and advantages will become apparent, in the following detailed description of preferred embodiments illustrated in the accompanying drawing, in which.

Figure 1:
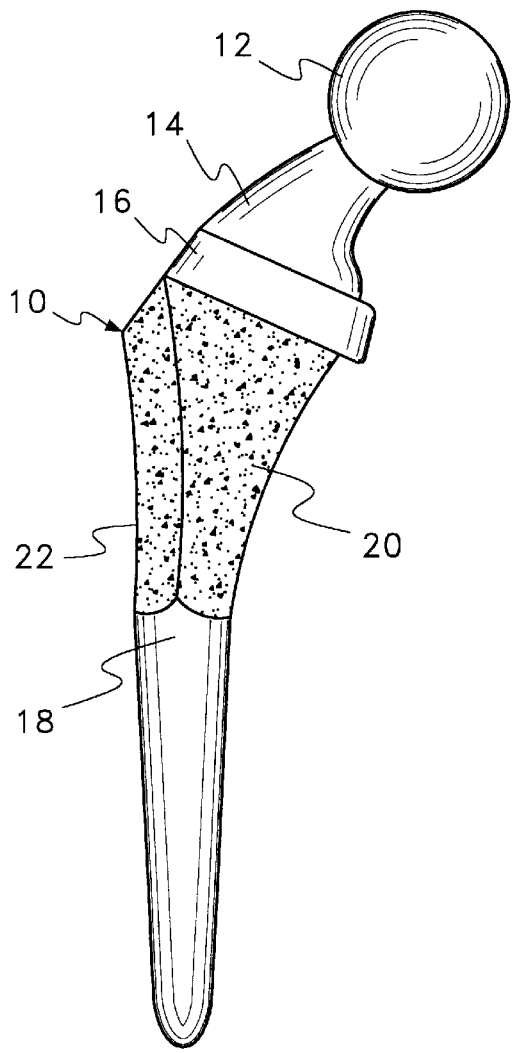
FIG. 1 is an elevational view of a metallic texture coated component of a prosthetic implant.

Referring now to the drawing, and especially to FIG. 1 thereof, a component of a prosthetic implant is illustrated in the form of a hip stem component 10 of a prosthetic hip replacement. The overall configuration of hip stem component 10 includes a conventional spherical head 12 carried by a neck 14 extending to a collar 16 between the neck 14 and a depending stem 18. In order to promote affixation of the stem 18 within the natural bone of a proximal femur (not shown), a metallic texture coating 20 is provided along a proximal portion 22 of the stem 18. In a typical conventional construction, the metallic texture coating 20 is commercially pure titanium, the stem 18 is constructed of a titanium alloy, and the metallic texture coating 20 is applied to the stem 18 by arc-deposition. Such arc-deposition of titanium on a titanium alloy substrate has been found to attain the desired characteristics in metallic texture coating 20 insofar as promoting affixation of the stem 18 within the natural bone.

Figure 2:
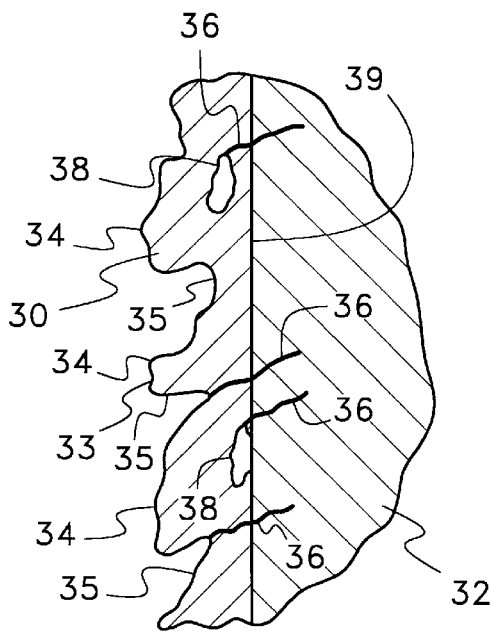
FIG. 2 is a largely diagrammatic, enlarged fragmentary cross-sectional view showing a metallic texture coating on a prosthetic implant component constructed in accordance with the prior art.

However, it has been observed that the use of a metallic texture coating of titanium arc-deposited directly upon a substrate of titanium alloy significantly decreases the fatigue strength of the substrate. Thus, as illustrated in FIG. 2, a metallic texture coating 30 has been arc-deposited upon a substrate 32 of an implant component constructed in accordance with the prior art, and includes an irregular surface profile 33 having a multiplicity of peaks 34 and valleys 35. The relatively small radii found in at least some of the valleys 35 become a source of fatigue-induced cracks 36 which, in time, propagate through the metallic texture coating 30 to the substrate 32, and into the substrate 32 to continue to progress through the substrate 32 to eventually cause catastrophic failure. In addition, voids 38, either within the metallic texture coating 30 or at the interface 39 between the metallic texture coating 30 and the substrate 32, likewise can be a source of fatigue-induced cracks 36.

Figure 3:
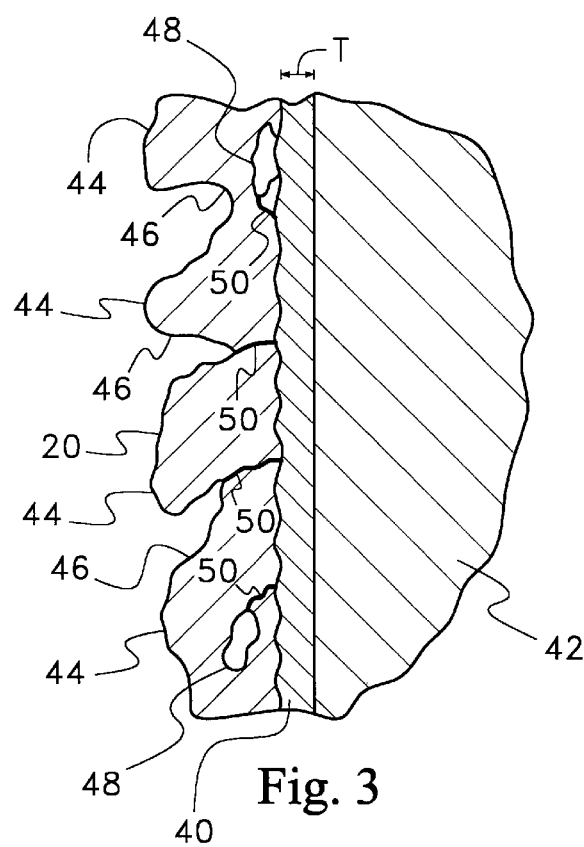
FIG. 3 is a largely diagrammatic, enlarged fragmentary cross-sectional view showing a metallic texture coating on a prosthetic implant component constructed in accordance with the present invention.

In order to defeat the fatigue failure mechanism described above in connection with FIG. 2, the present invention, as illustrated in FIG. 3, interposes a layer 40 of material between the metallic texture coating 20 and the substrate 42 of stem 18. The layer 40 is bonded to the substrate 42; that is, the layer 40 is adhered to the substrate 42 in intimate contact with the substrate 42. For example, a layer 40 of commercially pure titanium thermally-sprayed upon a substrate 42 of titanium alloy, as by plasma-spraying, is bonded intimately to the substrate 42 and provides the desired layer 40. The layer 40, in turn, receives the metallic texture coating 20 which is applied to the layer 40, as by arc-deposition, to adhere to the layer 40, and to the proximal portion 22 of the stem 18, to adequately serve the purpose for which the metallic texture coating 20 is employed. Metallic texture coating 20 has a multiplicity of peaks 44 and valleys 46, and includes voids 48, all as described above in connection with coating 30.

It has been found that any fatigue-induced cracks formed in the metallic texture coating 20, as illustrated at 50, are deterred by the layer 40 from propagating beyond the layer 40 and into the substrate 42 of the stem 18. Accordingly, by interposing layer 40 between the metallic texture coating 20 and the substrate 42 of the stem 18, the fatigue strength of the stem 18 is increased over the fatigue strength observed in the structure where metallic texture coating 30 is deposited directly on the substrate 32, as described above in connection with FIG. 2. Layer 40 may be a metallic material, such as commercially pure titanium plasma sprayed by conventional methods upon the substrate 32, or a ceramic material, such as titanium nitride. Preferably, the physical characteristics of the layer 40, such as thickness and density, are such that any contact between the metallic texture coating 20 and the substrate 42 which could permit the propagation of a fatigue-induced crack 50 through the metallic texture coating 20 and into the substrate 42 is precluded. Thus, for example, a layer 40 of plasma-sprayed commercially pure titanium having a thickness T of at least about fifty microns has been found to be effective. Further, the outer surface 48 of the layer 40 may be provided with a roughness sufficient to receive and adhere an arc-deposited metallic texture coating 20 to the stem 18 without the necessity for further treatment of the layer 40. The increase in fatigue strength attained by the use of layer 40 enables the employment of a metallic texture coating at certain locations on an implant component where a metallic texture coating heretofore has been avoided because of the structural demands placed upon the implant component at those locations. Thus, whereas metallic texture coatings heretofore have not been placed at locations which are relatively highly stressed during service and which therefore are susceptible to the onset of fatigue-induced cracks, it now becomes feasible to utilize metallic texture coatings, if desired, at such locations, thereby enabling a wider choice of design options in the construction of implant components.

It will be seen that the present invention attains the several objects and advantages summarized above; namely: Enables increased longevity in prosthetic implants having metallic texture coated components; provides metallic texture coated components of prosthetic implants with an improved structure which enhances fatigue strength, as compared to metallic texture coated components without the improved structure; attains the advantages of metallic texture coated prosthetic implant components without a detrimental reduction in the fatigue strength of the components; enables the use of desirable metallic texture coatings and techniques, such as arc-deposited titanium coatings, for components of a prosthetic implant without sacrificing long-term performance; enables the use of a metallic texture coating at locations on an implant component not previously amenable to a metallic texture coaling because of structural demands placed upon the component at those locations, thereby providing a wider choice of design options in the construction of implant components; provides a relatively simple technique for constructing a metallic texture coated prosthetic implant component having desirable fatigue strength characteristics.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A prosthetic implant component having a metallic texture coating on a substrate for enhancing fixation of the implant in natural bone, the prosthetic implant component comprising: a layer of material interposed between the metallic texture coating and the substrate for increasing the fatigue strength of the prosthetic implant component, the layer being bonded to the substrate and, in turn, receiving the metallic texture coating so as to deter propagation of fatigue-induced cracks from the metallic texture coating into the substrate.

2. The invention of claim 1 wherein the metallic texture coating is arc-deposited on the layer, and thus layer has a thickness sufficient to prevent the arc-deposited coating from contacting the substrate.

3. The invention of claim 1 wherein the material of the layer is a metallic material.

4. The invention of claim 1 wherein the material of the layer is a ceramic material.

5. The invention of claim 1 wherein the layer is a thermally-sprayed layer of titanium and the metallic texture coating is arc-deposited on the thermally-sprayed layer.

6. The invention of claim 1 wherein the layer is a plasma-sprayed layer of titanium and the metallic texture coating is arc-deposited on the plasma-sprayed layer.

7. The invention of claim 6 wherein the layer has a thickness of at least about fifty microns.

8. A method for increasing the fatigue strength of a prosthetic implant component having a metallic texture coating on a substrate, the method comprising: interposing a layer of material between the metallic texture coating and the substrate, with the layer being bonded to the substrate and, in turn, receiving the metallic texture coating so as to deter propagation of fatigue-induced cracks from the metallic texture coating into the substrate.

9. The invention of claim 8 wherein the metallic texture coating is arc-deposited on the layer in a thickness sufficient to prevent the arc-deposited coating from contacting the substrate.

10. The invention of claim 8 wherein the material of the layer is a metallic material.

11. The invention of claim 8 wherein the material of the layer is a ceramic material.

12. The invention of claim 8 wherein the layer is titanium and is thermally-sprayed onto the substrate, and the metallic texture coating is arc-deposited on the thermally-sprayed layer.

13. The invention of claim 8 wherein the layer is titanium and is plasma-sprayed onto the substrate, and the metallic texture coating is arc-deposited on the plasma-sprayed layer.

14. The invention of claim 13 wherein the layer is plasma sprayed to a thickness of at least about fifty microns.

\* \* \* \* \*